United States Patent
Osborne

(10) Patent No.: US 9,097,621 B2
(45) Date of Patent: Aug. 4, 2015

(54) TEST APPARATUS FOR PROVIDING AXIAL STRESSES IN A STRUCTURE

(71) Applicant: AIRBUS OPERATIONS LIMITED, Bristol (GB)

(72) Inventor: Richard William Osborne, Bristol (GB)

(73) Assignee: AIRBUS OPERATIONS LIMITED, Bristol (GB)

( * ) Notice: Subject to any disclaimer, the term of this patent is extended or adjusted under 35 U.S.C. 154(b) by 223 days.

(21) Appl. No.: 13/774,428

(22) Filed: Feb. 22, 2013

(65) Prior Publication Data

US 2013/0220024 A1  Aug. 29, 2013

(30) Foreign Application Priority Data

Feb. 23, 2012  (GB) .................................. 1203104.3

(51) Int. Cl.
   *G01N 3/20* (2006.01)
   *G01N 3/08* (2006.01)
   *G01M 5/00* (2006.01)

(52) U.S. Cl.
   CPC ................. *G01N 3/20* (2013.01); *G01M 5/005* (2013.01); *G01M 5/0075* (2013.01); *G01N 2203/0017* (2013.01); *G01N 2203/0019* (2013.01); *G01N 2203/0023* (2013.01); *G01N 2203/0254* (2013.01); *G01N 2203/0272* (2013.01); *G01N 2203/0282* (2013.01)

(58) Field of Classification Search
   CPC ............ G01N 3/00; G01N 3/02; G01N 3/08; G01N 3/20; G01N 2203/0019; G01N 2203/0023

USPC ........... 73/788, 818, 856, 790, 812, 813, 819, 73/831, 849

See application file for complete search history.

(56) References Cited

U.S. PATENT DOCUMENTS 4,552,024 A * 11/1985 Baker et al. ...................... 73/821
5,448,918 A *  9/1995 Tucchio ........................... 73/819

FOREIGN PATENT DOCUMENTS

| DE | 29706829 U1 | 6/1997 |
| DE | 19607713 A1 | 9/1997 |

(Continued)

OTHER PUBLICATIONS

Search Report corresponding to GB 1203104.3 dated Jun. 22, 2012.

(Continued)

*Primary Examiner* — Lisa Caputo
*Assistant Examiner* — Jonathan Dunlap
(74) *Attorney, Agent, or Firm* — Lowe Hauptman & Ham, LLP

(57) ABSTRACT

The invention provides a test apparatus for providing axial stresses in a structure, comprising a first set of formations for abutting a first surface of the structure at a first plurality of locations, a second set of formations for abutting a second surface of the structure at a second plurality of locations, and a force actuator, and wherein each set of formations comprises at least three formations and wherein at least two formations in each set of formations are aligned with a notional alignment line along the structure and at least one formation in each set of formations is out of alignment along the structure with said notional alignment line, such that when the force actuator applies a force, loads are applied at different locations, causing the structure to bend biaxially and thereby providing biaxial stresses in the structure.

12 Claims, 3 Drawing Sheets

(56) References Cited

FOREIGN PATENT DOCUMENTS

| DE | 102004048784 A1 | 4/2006 |
|---|---|---|
| FR | 2624605 A1 | 6/1989 |

OTHER PUBLICATIONS

European Search Report dated Jul. 11, 2013, issued in European Application No. 13156250.6.

\* cited by examiner

TEST APPARATUS FOR PROVIDING AXIAL STRESSES IN A STRUCTURE

RELATED APPLICATIONS

The present application is based on, and claims priority from, British Application No. 1203104.3, filed Feb. 23, 2012, the disclosure of which is hereby incorporated by reference herein in its entirety.

BACKGROUND OF THE INVENTION

The present invention concerns a test apparatus for providing axial stresses in a structure. More particularly, but not exclusively, this invention concerns a test apparatus for providing axial stresses in a structure, the structure having a first surface on one side and a second surface on an opposite side. The invention also concerns a method of providing axial stresses in a structure.

An existing test arrangement is shown in FIG. 1. The test arrangement 1 is testing a sandwich structure 10. The sandwich structure 10 has a top surface 11 and a bottom surface 12. The structure 10 is made up of a top skin 13, bottom skin 14 and a core 15. The test apparatus comprises a base structure 20, a top structure 30 and a load block 40.

The base structure 20 comprises a base platform 21 from which two upwardly extending formations 22, 23 extend. The formations 22, 23 are curved at their tip to minimise the lengthwise distance along which the load is applied. The formations 22, 23 extend along the width of the structure 10. On top of each formation 22, 23 grease 26 is applied to aid rotation, if large downward deflections of the structure 10 are expected. Then a Vee block 25 and then a rubber pad 26 are placed on top of the formations 22, 23. The Vee block 25 and rubber pad 26 reduce the through thickness stress exerted on the structure 10 at the formations 22, 23. The sandwich structure 10 is placed on top of the two rubber blocks 24.

The top structure 30 comprises a top platform 31 from which two downwardly extending formations 32, 33 extend. The formations 32, 33 are curved at their tip to minimise the lengthwise distance along which the load is applied. The formations 32, 33 extend along the width of the structure 10. On the end of each top formation 32, 33 grease 36 is applied to aid rotation, if large downward deflections of the structure 10 are expected. Then a Vee block 35 and then a rubber pad 36 are placed on the end of the formations 32, 33. The Vee block 35 and rubber pad 36 reduce the through thickness stress exerted on the structure 10 at the formations 32, 33. The top structure 30 is placed on top of the sandwich structure 10 so that the rubber pads 34 sit on the top surface 11 of the structure 10.

In use, the sandwich structure 10 is placed in between the upwardly extending and downwardly extending formations 22, 23, 32, 33 and a load block 40 is placed on the top of the top platform 31. This causes the structure 10 to bend downwards at all locations between the two upwardly extending formations 22, 23. Maximum downward bending occurs between the two downwardly extending formations 32, 33. Relative upward bending occurs at the outer portions of the structure 10 (either side of the two upwardly extending formations 22, 23). This creates uni-axial stresses (along a single axis) in the portion of the structure between the two downwardly extending formations 32, 33 and allows this portion to be tested. The maximum downwards deflection can be measured at the mid-point between the two downwardly extending formations 32, 33.

This test apparatus is normally used for thin skinned sandwich panel structures. This is because in these structures, the test produces near uniform uni-axial compressive stress on the top surface 11 and near uniform uni-axial tensile stress in the bottom surface 12. The bending moment and skin stresses are maximum and constant in between the two downwardly extending formations 32, 33. Through thickness shear forces are only produced on either side of the downwardly extending formations 32, 33. The test apparatus is normally used for sandwich structures with a lightweight (for example, honeycomb) core and thin composite (for example, fibre reinforced plastic or carbon prepreg) skins. In particular, the test works best if the core depth is over 6 times the skin thickness.

The test is used to investigate the strength of the sandwich skins. Therefore, ideally the load used and the formation positions are designed to ensure skin failure (prior to core shear failure).

The test rig is simple and can be used by using only a single downward load 40.

However, it is often desired to test a structure by applying bi-axial loads. Currently, this can be done by attaching an actuator to each of four different legs of a cruciform structure, and applying a pulling or pushing force to each actuator. However, these bi-axial rigs require a complex calibration to confirm the biaxial loads in the structure compared to the forces applied at the actuators. This is because, the actuator on one leg, even if no force is applied to it, constrains the leg and affects the stress in the structure due to Poisson deformation being prevented. This makes bi-axial testing complicated, costly and time-consuming.

The present invention seeks to mitigate the above-mentioned problems. Alternatively or additionally, the present invention seeks to provide an improved test apparatus for and method of providing bi-axial stresses in a structure.

SUMMARY OF THE INVENTION

The present invention provides, according to a first aspect, a test apparatus for providing axial stresses in a structure, the structure having a first surface on one side and a second surface on an opposite side, wherein the test apparatus comprises a first set of formations for abutting the first surface of the structure at a first plurality of locations on the structure, a second set of formations for abutting the second surface of the structure at a second plurality of locations on the structure, the first and second plurality of locations defining different footprints, and a force actuator for applying a force which urges at least one of the first and second set of formations towards the other set, and wherein each set of formations comprises at least three formations and wherein at least two formations in each set of formations are aligned with a notional alignment line along the structure and at least one formation in each set of formations is out of alignment along the structure with said notional alignment line, such that when the force actuator applies the force which urges at least one of the first and second set of formations towards the other set, loads are applied at different locations over each notional alignment line and at a further location out of alignment with each notional alignment line, causing the structure to bend biaxially and thereby providing biaxial stresses in the structure.

Having out of alignment formations allows bi-axial bending to be produced whilst only applying load through a single force actuator. Hence, embodiments of the invention have the advantage of having the same simple load interaction of the test rig shown in FIG. 1 whilst still providing bi-axial stresses in the structure. This could enable better understanding of bi-axial stress failure envelopes, refinement of bi-axial stress analysis and improve weight optimisation of, for example, composite structures. This is especially advantageous when sandwich panel structures or monolithic I-beam structures are being considered. The test apparatus is easier to maintain and set up than other apparatus for providing bi-axial stresses, as there is only one actuator and no bolting is required. It also means that open hole and impact damaged structures could be tested with bi-axial stresses. This could improve method refinement for calculating allowable damage under bi-axial loading and could lead to improved maintenance of, for example, composite structures.

Preferably, the footprints of the first and second sets of formations are entirely different. In other words, preferably, none of the first plurality of locations corresponds to any of the second plurality of locations.

Preferably, the force actuator is for applying a force which urges all formations in at least one of the first and second set of formation towards all formations of the other set.

Preferably, each set of formations comprises four formations and wherein the four formations comprise a first pair of formations aligned along a first notional alignment line and a second pair of formations aligned along a second notional alignment line, and wherein the first and second alignment lines are at an angle to each other. This provides a more stable arrangement.

More preferably, the first pair of formations of the first set of formations are aligned along the same first notional alignment line as the first pair of formations of the second set of formations and wherein the second pair of formations of the first set of formations are aligned along the same second notional alignment line as the second pair of formations of the second set of formations. This provides bi-axial bending along two defined axes.

Preferably, the first formation of the first pair of formations lies to one side of the second alignment line and the second formation of the first pair of formations lies to the other side of the second alignment line and wherein the first formation of the second pair of formations lies to one side of the first alignment line and the second formation of the second pair of formations lies to the other side of the first alignment line. This provides bi-axial loading in a cruciform/cross shape.

Preferably, the first alignment line is transverse, preferably, approximately perpendicular, to the second alignment line. This provides bi-axial loading in a cross shape, with 4 arms, each at 90 degrees to each other.

Preferably, each formation is rigid. In other words, preferably, each formation does not substantially depress under loading.

Preferably, each formation is elongate and arranged to provide a line of contact along the length of the formation. Preferably, each formation is arranged to provide a line of contact with the structure and wherein the line of contact of each formation is approximately perpendicular to its notional alignment line. This provides a more stable arrangement.

Optionally, for a first set of formations, the footprints of the formations of the first and second pairs of formations are arranged to be located around a first point, whereas, in the second set of formations, the footprints of the formations of the first and second pairs of formations are arranged to be located further away from that point. This provides equal sign biaxial bending, with the first surface of the structure under compression and the second surface of the structure under tension.

Alternatively, for a first set of formations, the footprints of the formations of the first pair of formations are arranged to be located around a first point, and the footprints of the formations of the second pair of formations are arranged to be located further away from that point, whereas, in the second set of formations, the footprints of the formations of the first pair of formations are arranged to be located further away from that point, and the footprints of the formations of the second pair of formations are arranged to be located around the first point. This provides opposite sign biaxial bending. Preferably, the first pair of formations of the first set of formations are aligned along the same notional alignment line as the second pair of formations of the second set of formations and wherein the second pair of formations of the first set of formations are aligned along the same notional alignment line as the first pair of formations of the second set of formations.

According to the first aspect of the invention, there is also provided a test rig for use with the test apparatus described above, wherein the test rig comprises a base, and a set of at least three formations attached to the base, wherein at least one formation in the set of formations is out of alignment along the base from other formations.

Preferably, the formations are movably mounted on the base such that the locations of the formations along the base are adjustable. This allows the load magnitudes in each direction to be tailored to the test required.

According to the first aspect of the invention, there is also provided a structure for testing with the test apparatus as described above or the test rig as described above, wherein the structure comprises a central test portion and at least three legs extending away from the central test portion.

Preferably, the structure is in the shape of a cruciform.

Preferably, the structure is a sandwich panel structure or an I-beam structure.

According to a second aspect of the invention, there is also provided a method of providing axial stresses in a structure, the structure having a first surface on one side and a second surface on an opposite side, wherein the method comprises the following steps providing a first set of at least three formations for abutting the first surface of the structure at a first plurality of locations on the structure, wherein at least two formations in the first set of formations are aligned with a first notional alignment line along the structure and at least one formation in the first set of formations is out of alignment along the structure with said first notional alignment line, providing a second set of at least three formations for abutting the second surface of the structure at a second plurality of locations on the structure, the first and second plurality of locations defining different footprints, wherein at least two formations in the second set of formations are aligned with a second notional alignment line along the structure and at least one formation in the second set of formations is out of alignment along the structure with said second notional alignment line, placing the structure to be tested in between the two sets of formations, applying a force to urge at least one of the first and second set of formations towards the other set, causing loads to be applied at different locations over each notional alignment line and at a further location out of alignment with each notional alignment line, causing the structure to bend biaxially and thereby providing biaxial stresses in the structure.

It will of course be appreciated that features described in relation to one aspect of the present invention may be incorporated into other aspects of the present invention. For example, the method of the invention may incorporate any of the features described with reference to the apparatus of the invention and vice versa.

DESCRIPTION OF THE DRAWINGS

Embodiments of the present invention will now be described by way of example only with reference to the accompanying schematic drawings of which.

DETAILED DESCRIPTION

Figure 1:
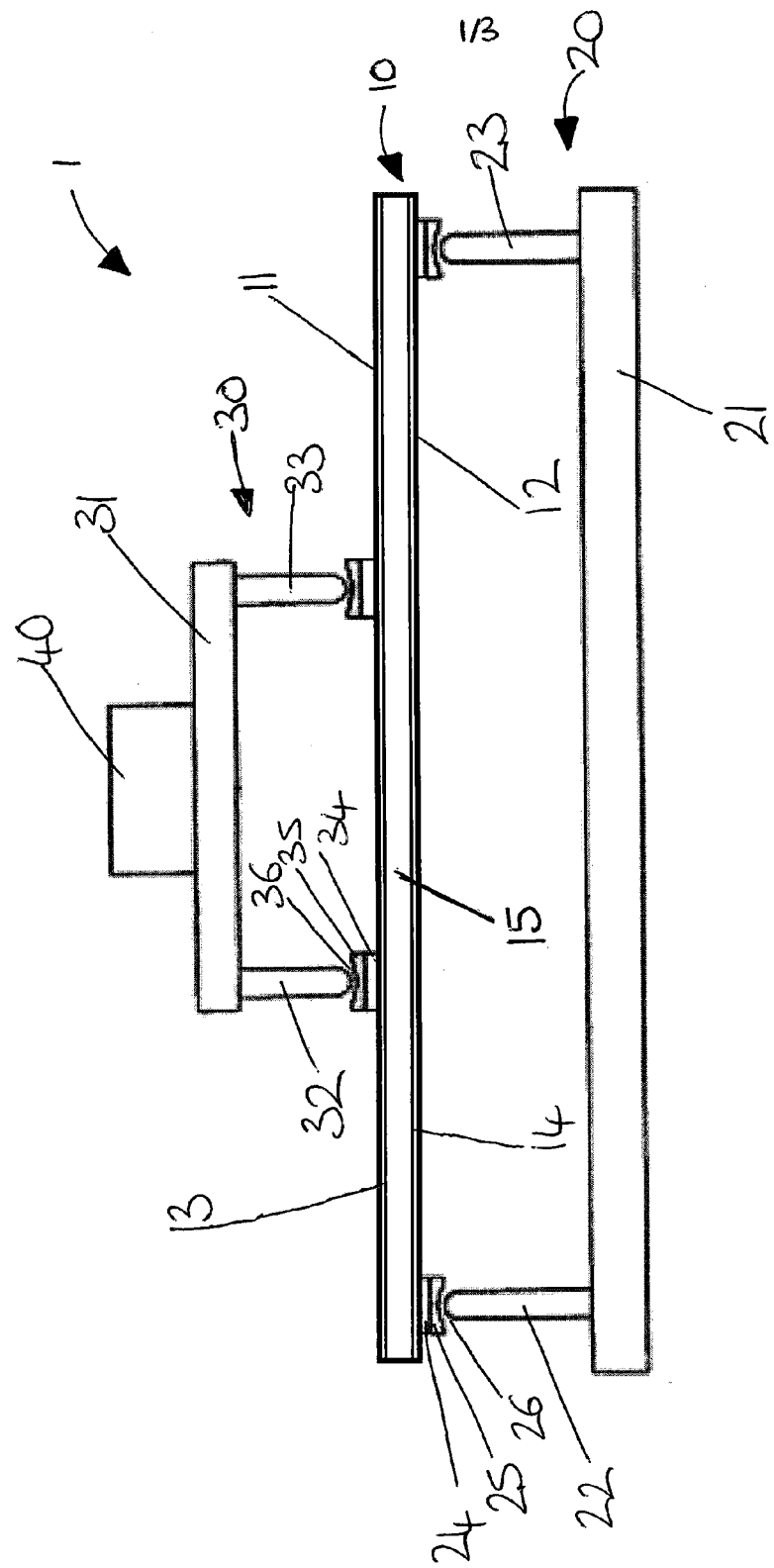
FIG. 1 shows a side sectional view of a prior art test arrangement.
Figure 2:
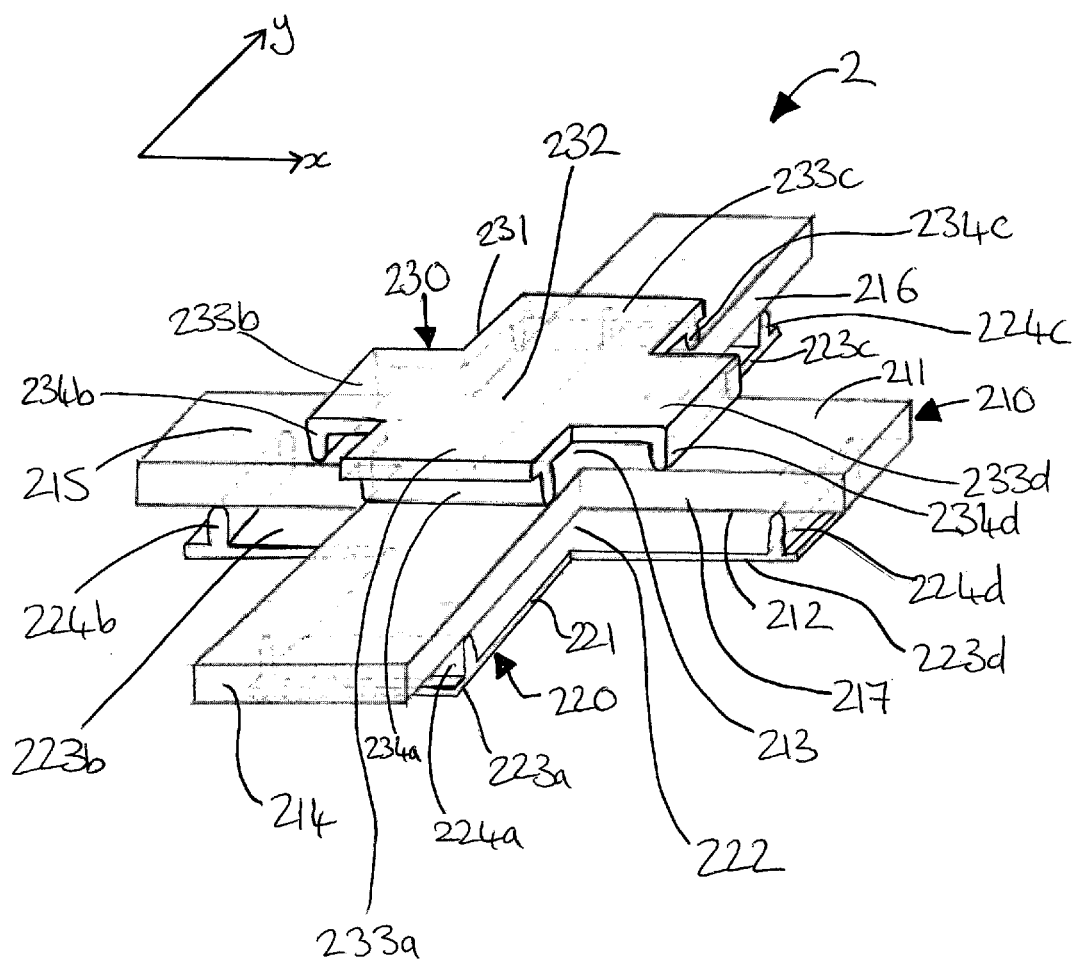
FIG. 2 shows a perspective view of a test arrangement according to a first embodiment of the invention.

FIG. 2 shows a perspective view of a test arrangement 2 according to a first embodiment of the invention. The test arrangement 2 is testing a sandwich structure 210. The sandwich structure 210 has a top surface 211 and a bottom surface 212. The structure 210 is in the form of a slender symmetrical cruciform shape with a central portion 213 and four legs 214, 215, 216, 217 at 90 degrees to each other.

The test apparatus comprises a base structure 220, a top structure 230 and a load block (not shown).

The base structure 220 comprises a base platform 221 in the form of a slender symmetrical cruciform shape. The base platform 221 has a central portion 222 and four legs 223a, 223b, 223c, 223d at 90 degrees to each other. Towards the far end of each leg 223, there is an upwardly extending formation 224a, 224b, 224c, 224d across the width of each leg 223. The sandwich structure 210 is placed on top of the four upwardly extending formations 224 such that each leg is resting on one of the upwardly extending formations. The widths of the legs 214, 215, 216, 217 of the structure 210 are narrower than the length of the upwardly extending formations 224.

The top structure 230 comprises a top platform 231 in the form of a squat symmetrical cruciform shape. The base platform 231 has a central portion 232 and four short legs 233a, 233b, 233c, 233d at 90 degrees to each other. Towards the far end of each leg 233, there is a downwardly extending formation 234a, 234b, 234c, 234d across the width of each leg 233. The top structure 230 is placed on top of the sandwich structure 210 so that the downwardly extending formations 234 sit on the top surface 211 of the structure 210. The downwardly extending formations 234 rest on the structure 210 towards the central portion 213, whereas the upwardly extending formations 224 rest on the structure 210 towards the far end of the legs 214, 215, 216, 217. The widths of the legs 214, 215, 216, 217 of the structure 210 are narrower than the length of the downwardly extending formations 234.

In use, the sandwich structure 210 is placed in between the upwardly extending and downwardly extending formations 224, 234 and a load block (not shown) is placed on the top of the top platform 231. This causes the structure 210 to bend downwards in both directions between the upwardly extending formations 224 and upwards at its outer portions (in both directions outside of the upwardly extending formations 224). Maximum downward bending occurs in the central portion 213 (in both directions between the downwardly extending formations 234). This creates bi-axial stresses (along both the x and y axes) in the central portion 213 of the structure. In particular, in the central portion 213, the upper skin of the structure 210 is exposed to equal sign biaxial compression (i.e. compression in both the x and y axes) and the lower skin of the structure 210 is exposed to equal sign biaxial tension (i.e. tension in both the x and y axes).

Figure 3:
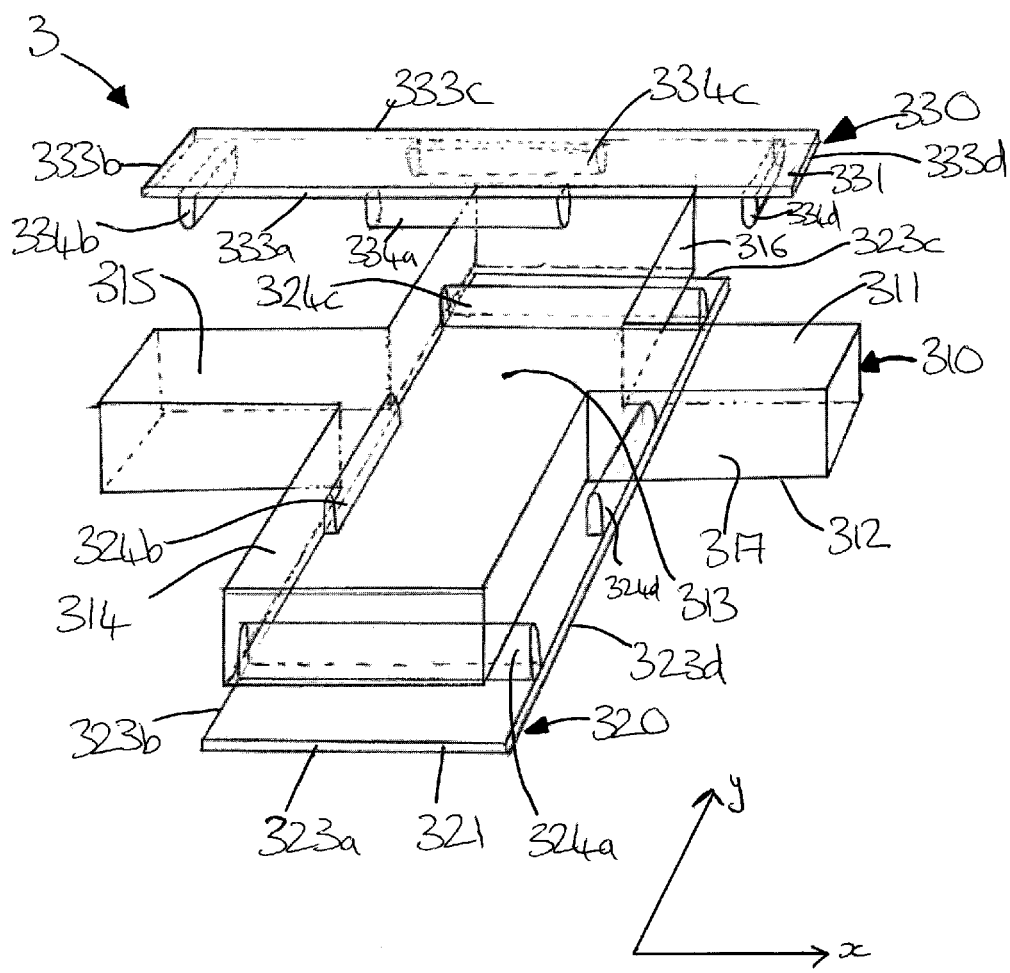
FIG. 3 shows a partly exploded perspective view of a test arrangement according to a second embodiment of the invention.

FIG. 3 shows a partly exploded perspective view of a test arrangement 3 according to a second embodiment of the invention. The test arrangement 3 is testing a sandwich structure 310. The sandwich structure 310 has a top surface 311 and a bottom surface 312. The structure 310 is in the form of a slender symmetrical cruciform shape with a central portion 313 and four legs 314, 315, 316, 317 at 90 degrees to each other.

The test apparatus comprises a base structure 320, a top structure 330 and a load block (not shown).

The base structure 320 comprises a base platform 321 in the form of a rectangular shape with two long sides 323b, 323d along its length (in the direction of the y axis) and two short sides 323a, 323c along its width (in the direction of the x axis). On each long side 323b, 323d there is an upwardly extending elongate formation 324b, 324d extending along the middle portion of the long side 323b, 323d. Towards each short side 323a, 323c there is an upwardly extending elongate formation 324a, 324c extending across the width of the base platform 321. The sandwich structure 310 is placed on top of the four upwardly extending formations 324 such that each leg is resting on one of the upwardly extending formations, with opposite legs 314 and 316 being supported by upwardly extending formations 324a, 324c towards the end of the legs and opposite legs 315 and 317 being supported by upwardly extending formations 324b, 324d towards the central portion 313. The widths of the legs 314, 315, 316, 317 of the structure 310 are narrower than the length of the upwardly extending formations 324.

The top structure 330 comprises a top platform 331 in the form of a rectangular shape with two long sides 333a, 333c along its length and two short sides 333b, 333d along its width. On each long side 333a, 333c there is a downwardly extending elongate formation 334a, 334c extending along the middle portion of the long side 333a, 333c. Towards each short side 333b, 333d there is a downwardly extending elongate formation 334b, 334d extending across the width of the top platform 331.

The top structure 330 is placed on top of the sandwich structure 310 and base structure 320 such that the length of the top platform 331 is perpendicular to the length of the base platform 321 (i.e. the length of the top platform 331 is in the direction of the x axis) and so that each downwardly extending formation 334 rests on one of the legs 314, 315, 316, 317 of the structure 310. The downwardly extending formations 334a, 334c rest on the structure 310 towards the central portion 313 on legs 314 and 316, whereas the downwardly extending formations 334b, 334d rest on the structure 310 towards the far ends of legs 315 and 317. The upwardly extending formations 324b, 324d support the structure 310 towards the central portion 313 on legs 315 and 317, whereas the upwardly extending formations 324a, 324c support the structure 310 towards the far ends of legs 314 and 316. The widths of the legs 314, 315, 316, 317 of the structure 310 are narrower than the length of the downwardly extending formations 334.

In use, the sandwich structure 310 is placed in between the upwardly extending and downwardly extending formations 324, 334 and a load block (not shown) is placed on the top of the top platform 331. This causes the structure 310 to experience bi-axial stresses (along both the x and y axes) in the central portion 313 of the structure. In particular, in the central portion 313, the upper skin of the structure 310 is exposed to opposite sign biaxial compression (i.e. tension in the x axis and compression in the y axis) and the lower skin of the structure 310 is exposed to opposite sign biaxial tension (i.e. tension in the y axis and compression in the x axis).

A disadvantage of the embodiment shown in FIG. 3 is that the test arrangement is "top-heavy" and may require a way of stabilising the top structure 320.

In both embodiments, the cruciform sandwich structures 210, 310 could be made by forming a large square sandwich panel and cutting out squares from each corner of that large square to form the cruciform shape. The cut-off square could be used for a number of different uses, for example in process control tests, use as travelers or use in destructive examination quality checks.

Whilst the present invention has been described and illustrated with reference to particular embodiments, it will be appreciated by those of ordinary skill in the art that the invention lends itself to many different variations not specifically illustrated herein. By way of example only, certain possible variations will now be described.

The test apparatuses could be used to test other types of structures, such as thin webbed monolithic I-beams. This would enable bi-axial stress testing on a monolithic laminate. It could also be used for box beam structures or any other structure with similar behaviour.

The base structures 220, 230 and top structures 230, 330 may be modified to allow the formations 234, 334 to be moved. This allows for the possibility of varying the relative magnitude of the biaxial skin stress in one direction (x axis) compared to the other (y axis), whilst still using a single test apparatus.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A test apparatus for providing axial stresses in a structure, the structure having a first surface on one side and a second surface on an opposite side, wherein the test apparatus comprises:
    a first set of formations for abutting the first surface of the structure at a first plurality of locations on the structure,
    a second set of formations for abutting the second surface of the structure at a second plurality of locations on the structure, the first and second plurality of locations defining different footprints, and
    a force actuator for applying a force which urges at least one of the first and second set of formations towards the other set, and
    wherein each set of formations comprises at least three formations and wherein at least two formations in each set of formations are aligned with a notional alignment line along the structure and at least one formation in each set of formations is out of alignment along the structure with said notional alignment line,
    such that when the force actuator applies the force which urges at least one of the first and second set of formations towards the other set, loads are applied at different locations over each notional alignment line and at a further location out of alignment with each notional alignment line, causing the structure to bend biaxially and thereby providing biaxial stresses in the structure, wherein each set of formations comprises four formations and wherein the four formations comprise a first pair of formations aligned along a first notional alignment line and a second pair of formations aligned along a second notional alignment line, and wherein the first and second alignment lines are at an angle to each other, and wherein each formation is arranged to provide a line of contact with the structure and wherein the line of contact of each formation is approximately perpendicular to its notional alignment line.

2. A test apparatus as claimed in claim 1, wherein the first pair of formations of the first set of formations are aligned along the same first notional alignment line as the first pair of formations of the second set of formations and wherein the second pair of formations of the first set of formations are aligned along the same second notional alignment line as the second pair of formations of the second set of formations.

3. A test apparatus as claimed in claim 1, wherein the first formation of the first pair of formations lies to one side of the second alignment line and the second formation of the first pair of formations lies to the other side of the second alignment line and wherein the first formation of the second pair of formations lies to one side of the first alignment line and the second formation of the second pair of formations lies to the other side of the first alignment line.

4. A test apparatus as claimed in claim 1 wherein the first alignment line is approximately perpendicular to the second alignment line.

5. A test apparatus as claimed in claim 1, wherein, for a first set of formations, the footprints of the formations of the first and second pairs of formations are arranged to be located around a first point, whereas, in the second set of formations, the footprints of the formations of the first and second pairs of formations are arranged to be located further away from that point.

6. A test apparatus as claimed in claim 1, wherein, for a first set of formations, the footprints of the formations of the first pair of formations are arranged to be located around a first point, and the footprints of the formations of the second pair of formations are arranged to be located further away from that point, whereas, in the second set of formations, the footprints of the formations of the first pair of formations are arranged to be located further away from that point, and the footprints of the formations of the second pair of formations are arranged to be located around the first point.

7. A structure for testing with the test apparatus as claimed in claim 1, wherein the structure comprises a central test portion and at least three legs extending away from the central test portion.

8. A structure as claimed in claim 7, wherein the structure is in the shape of a cruciform.

9. A structure as claimed in claim 7, wherein the structure is a sandwich panel structure or an I-beam structure.

10. A test rig for use with the test apparatus of claim 1, wherein the test rig comprises:
    a base, and
    a set of at least three formations attached to the base, wherein at least one formation in the set of formations is out of alignment along the base from the formations.

11. A test rig as claimed in claim 10, wherein the formations are movably mounted on the base such that the locations of the formations along the base are adjustable.

12. A method of providing axial stresses in a structure, the structure having a first surface on one side and a second surface on an opposite side, wherein the method comprises the following steps:
    providing a first set of four formations for abutting the first surface of the structure at a first plurality of locations on the structure, wherein a first pair of formations in the first set of formations are aligned with a first notional alignment line along the structure and a second pair of formations in the first set of formations are aligned with a second notional alignment line, at an angle to said first notional alignment line, providing a second set of four formations for abutting the second surface of the structure at a second plurality of locations on the structure, the first and second plurality of locations defining different footprints, wherein a first pair of formations in the second set of formations are aligned with a third notional alignment line along the structure and a second pair of formations in the second set of formations are aligned with a fourth notional alignment line, at an angle to said third notional alignment line, wherein each formation is arranged to provide a line of contact with the structure and wherein the line of contact of each formation is approximately perpendicular to its notional alignment line, placing the structure to be tested in between the two sets of formations, applying a force to urge at least one of the first and second set of formations towards the other set, causing loads to be applied at different locations over each notional alignment line, causing the structure to bend biaxially and thereby providing biaxial stresses in the structure.

* * * * *